(12) United States Patent
Kirchgaessler et al.

(10) Patent No.: US 11,609,213 B2
(45) Date of Patent: Mar. 21, 2023

(54) METHOD AND KIT FOR DETECTION OF CYANIDE

(71) Applicant: CYANOGUARD AG, Waedenswil (CH)

(72) Inventors: Benedikt Fabian Quirin Kirchgaessler, Waedenswil (CH); Mathias Cherbuin, Riehen (CH); Marjorie Sonnay, Zurich (CH)

(73) Assignee: CYANOGUARD AG, Waedenswil (CH)

( * ) Notice: Subject to any disclaimer, the term of this patent is extended or adjusted under 35 U.S.C. 154(b) by 209 days.

(21) Appl. No.: 16/612,854

(22) PCT Filed: May 12, 2018

(86) PCT No.: PCT/IB2018/053325
§ 371 (c)(1),
(2) Date: Nov. 12, 2019

(87) PCT Pub. No.: WO2018/211392
PCT Pub. Date: Nov. 22, 2018

(65) Prior Publication Data
US 2020/0150101 A1 May 14, 2020

(30) Foreign Application Priority Data
May 13, 2017 (GB) .................................. 1707710

(51) Int. Cl.
*G01N 31/22* (2006.01)
*C07H 23/00* (2006.01)

(52) U.S. Cl.
CPC ............ *G01N 31/22* (2013.01); *C07H 23/00* (2013.01)

(58) Field of Classification Search
CPC ................................ G01N 31/22; C07H 23/00
See application file for complete search history.

(56) References Cited

U.S. PATENT DOCUMENTS

| 4,144,306 A * | 3/1979 | Figueras ................. G01N 33/04 436/95 |
| 2003/0175846 A1* | 9/2003 | Parsons ................. C12N 9/0006 435/25 |
| 2009/0289213 A1* | 11/2009 | Pipper ..................... C07K 1/22 252/62.51 R |
| 2011/0033540 A1* | 2/2011 | Daniloff ................... A61L 27/20 424/484 |

FOREIGN PATENT DOCUMENTS

| CN | 102507577 A | 6/2012 |
| WO | WO-95/05598 A1 | 2/1995 |
| WO | WO-2011/116006 A2 | 9/2011 |
| WO | WO 2012/136793 A1 | 10/2012 |

OTHER PUBLICATIONS

Corresponding International Application No. PCT/IB2018/053325—International Search Report, dated Aug. 28, 2018.
Corresponding International Application No. PCT/IB2018/053325—International Written Opinion, dated Aug. 28, 2018.
Corresponding Great Britain Application No. GB 1707710.8—Search Report, dated Aug. 21, 2017.
Jian Ma, et al., "Cobinamide-Based Cyanide Analysis by Multiwavelength Spectrometry in a Liquid Core Waveguide", Analytical Chemistry, Jul. 15, 2010, pp. 6244-6250, vol. 82, No. 14.
William C. Blackledge, et al., "A New Facile Method to Measure Cyanide in Blood", Analytical Chemistry, May 15, 2010, pp. 4216-4221, vol. 82, No. 10.
Environmental Protection Agency, "Method 9014: Cyanide in Waters and Extracts Using Titrimetric and Manual Spectrophotometric Procedures", Hazardous Waste Test Methods/SW-846, Jul. 2014.
Yang, et al., "An Acridinium Salt-Based Fluorescent and Colorimetric Chemosensor for the Detection of Cyanide in Water", Organic Letters, Nov. 11, 2006, vol. 8, Issue 25, pp. 5721-5723, American Chemical Society.
Zelder, "Specific colorimetric detection of cyanide triggered by a conformational switch in vitamin $B_{12}$", Inorganic Chemistry, 2008, pp. 1264-1266, vol. 47, Issue 4, American Chemical Society.
Cho, et al., "The Benzil-Cyanide Reaction and its Application to the Development of a Selective Cyanide Anion Indicator", J. Am. Chem. Soc., Aug. 14, 2008, pp. 12163-12167, vol. 130, Issue 36.
Badugu, et al., et al., "Enhanced Fluorescence Cyanide Detection at Physiologically Lethal Levels: Reduced ICT-Based Signal Transduction", J. Am. Chern. Soc., Feb. 16, 2005, pp. 3635-3641, vol. 127, Issue 10.
"An Overview and Comparison of Methods for Cyanide Analysis", Presented at: 2009 Pittsburgh Conference on Analytical Chemistry and Applied Spectroscopy on Mar. 8-13, 2009.
Mannel-Croise, et al., "Side Chains of Cobalt Corrinoids Control the Sensitivity and Selectivity in the Colorimetric Detection of Cyanide", Inorganic Chemistry, Jan. 22, 2009, pp. 1272-1274, vol. 48, American Chemical Society.
La Brooy, et al., "Review of Gold Extraction from Ores", Minerals Engineering, Oct. 1994, pp. 1213-1241, vol. 7, Issue 10, Elsevier Science Ltd., Great Britain.
Yongyi Lou, et al., "Determination of cyanide in water", Journal of Preventive Medicine Information, vol. 4, No. 5, pp. 287-291, Dec. 31, 1988.
Badugu, et al., et al., "Enhanced Fluorescence Cyanide Detection at Physiologically Lethal Levels: Reduced ICT-Based Signal Transduction", J. Am. Chem. Soc., Feb. 16, 2005, pp. 3635-3641, vol. 127, Issue 10.

* cited by examiner

*Primary Examiner* — Brian R Gordon
*Assistant Examiner* — Dwan A Gerido
(74) *Attorney, Agent, or Firm* — Curatolo Sidoti & Trillis Co., LPA; Salvatore A. Sidoti; Floyd Trillis, III

(57) ABSTRACT

A metal contamination detection system, forming part of a cyanide detection system which is especially useful when used in conjunction with a corrinoid cyanide detection system as it allows for the quick and accurate assessment of impurities that could lead to a false cyanide result, and therefore the need to remove the impurities for an accurate result or a better metals recovery.

3 Claims, No Drawings

METHOD AND KIT FOR DETECTION OF CYANIDE

CROSS REFERENCE TO RELATED APPLICATIONS

This application is a national stage application of International Application No. PCT/IB2018/053325, filed 12 May 2018, which claims priority from Great Britain Patent Application No. 1707710.8, filed 13 May 2017, which applications are incorporated herein by reference.

This disclosure relates to the detection of cyanide and to methods for doing so. More particularly, it relates to the detection of impurities that could give false results.

Cyanide compounds are essential substances in a variety of industrial applications. A number of industrial processes produce substantial quantities of cyanides. There have been cases of accidental release into the environment, a major problem given the toxicity of cyanides. The problem is compounded by the fact that cyanide pollution is difficult to measure—according to the US EPA, only oil and grease pollution are more difficult. Quick and accurate methods of cyanide detection are therefore very important.

The US Environmental Protection Agency has a quantitative test method 1904 "Cyanide in waters and extracts using titrimetric and manual spectrophotometric procedures". However, a quick qualitative test is desirable, to ascertain whether there are cyanide ions present. There are a number of these. Some examples include Yang et al, *Org. Lett.* 2006, 25, 5721-5723) (hydrogen bonding), Zelder, *Inorg. Chem.* 2008, 47, 1264-1266 (metal coordination), Cho et al, *J. Am. Chem. Soc.* 2008; 130, 12163-12167 (bond-forming reactions between the nucleophilic cyanide and an electrophilic carbon) and Badugu et al, *J. Am. Chem. Soc.* 2005, 127, 3635-3641 (bond-forming reactions between the nucleophilic cyanide and a boron centre). A general reference "An overview and comparison of methods for cyanide analysis" was presented at the 2009 Pittsburgh Conference on analytical Chemistry and applied spectroscopy in March 2009.

More recently, there has been a method utilizing cobalt-containing corrinoid complexes, that is, compounds with this corrin skeleton

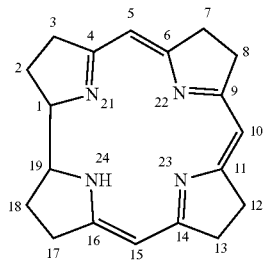

and with cobalt as the metal ion. These have proved effective as cyanide ion detectors The affinity of cyanide to corrinoids has been known for some time (Männel-Croisé et al *Inorg. Chem.* 2009; 48, 1272-1274 and in PCT publication WO 2012/136793).

While this method has proved interesting, there have been problems arising with the use of buffer solutions to maintain a steady pH, ideally at around 9.0-10.0, necessary for correct implementation of the Männel-Croisé method, are mentioned below. Typical suitable buffers include N-cyclohexyl-2-aminoethanesulfonic acid (CHES) and 4-(2-hydroxyethyl)-1-piperazineethanesulfonic acid (Hepes). The use of these liquid buffers can introduce problems. For example, the resulting dilution can change the sample matrix and lead to false results.

A further problem is that certain metal ions, for example, $Co^{2+}$, $Fe^{2+}$ $Fe^{2+}$, $Zn^{2+}$, $Cu^{2+}$ and $Ni^{2+}$, can form thermodynamically stable complexes with cyanide. This removes free cyanide from a sample under test. The only way to avoid false results in such circumstances is to utilise other processes, which is inconvenient and invariably slows down the detection process, making rapid detection nearly impossible.

The concentrations of such metal ions are relatively high, as shown in the following table of typical concentrations in plating baths:

TABLE 1

Typical Chemical Compositions of the Plating Baths used in Hong Kong

| Type of plating | Plating bath composition | |
|---|---|---|
| Copper | Copper cyanide | 20-25 g/l |
| | Sodium cyanide | 30-35 g/l |
| | Sodium carbonate | 15-30 g/l |
| Nickel | Nickel sulphate | 240-300 g/l |
| | Nickel chloride | 45-60 g/l |
| | Boric acid | 30-40 g/l |
| Chromium | Chromic acid anhydride | 250-400 g/l |
| | Sulphuric acid | 2.5-4.0 g/l |
| Zinc | Zinc metal | 25-45 g/l |
| | Sodium cyanide | 35-105 g/l |
| | Sodium hydroxide | 35-115 g/l |
| Tin | Stannous sulphate | 30-50 g/l |
| | Sulphuric acid | 40-70 g/l |
| | Phenolsulphuric acid | 30-60 g/l |
| Tin-Lead | Stannous sulphate | 12-20 g/l |
| | Lead | 8-14 g/l |
| | Fluoboric acid | 350-500 g/l |
| Gold | Potassium gold cyanide | 1-6 g/l |
| | Potassium cyanide | 30 g/l |
| Silver | Silver cyanide | 36-75 g/l |
| | Potassium cyanide | 60-90 g/l |
| Aluminium anodizing | Sulphuric acid | 15-25% (wt) |

(Source: Chiu et al, Water Poll. Control, Vol. 86, No. 1, 12-17 (1987)).

The presence of such ions is also a problem in the cyanide-based recovery of precious metals, such as gold, silver and platinum. It is well known that certain ions, particularly copper, that can be present in precious metal recovery processes, consume cyanide. It is described, for example, by La Brooy et al (*Minerals Engineering*, Vol. 7, No. 10, pp. 1213-1241 (1994) at p. 1218). This reduces the efficiency and therefore the profitability of the recovery process.

It has now been found that these problems can be substantially overcome by means of a revised method. There is therefore provided, as part of a cyanide detection system, a metal contamination detection system comprising a solid buffer, which pH has been adjusted to reach a value from 9 to 10.

There is additionally provided a method of detecting metal contamination in a cyanide detection system, comprising adding a test sample to a solid buffer prior to testing for cyanide.

The use of a solid buffer brings two advantages:
(a) It causes no dilution, meaning that any result is not altered;

(b) Any cyanide-complexed metal ions present will show up as a precipitate, indicating that action need be taken to remove them prior to the actual cyanide test.

Any buffer that can be prepared in solid form may be used in the detection system. Particular examples are carbonate (carbonate-bicarbonate) buffer, glycine buffer, AMP (2-amino-2-methyl-1-Propanol) buffer, AMPD (2-Amino-2-methyl-1,3-propanediol) buffer and CHES, more particularly CHES.

The buffer is prepared by lyophilisation of a liquid buffer. The preparation of such a buffer may be performed by any means known to the skilled person. Details of a particular preparation may be found in the following examples, but these are purely exemplary and are not intended to be in any way limiting. The pH that the buffer provides and stabilises is from 9-10. Particularly about 9.5

In use, the sample to be tested is dissolved in water and the solution added to the solid buffer. The formation of a precipitate indicates the presence of metal contamination, and this means that other art-recognised methods must be used to remove the metals prior to testing.

The method is particularly effective when used in conjunction with the Männel-Croisé corrinoid method hereinabove defined. The Männel-Croisé method is performed using a buffer in the pH range between 9 to 10, meaning that, if no metals are detected, the buffer solution used for metal detection can be immediately tested, something that is not possible with many other cyanide-testing methods. Together the two provide a simple, easily-performed test method for cyanide and metal contamination that could lead to false results in cyanide detection. There is therefore also provided a cyanide detection kit comprising (i) a metal contamination detection component comprising a solid buffer and (ii) a cyanide detection component, comprising: at least one first colorimetric solid phase extraction device, said first device comprising a non-polar solid phase loaded with a first corrinoid compound selected from the group consisting of: a cobalamine according to formula (I),

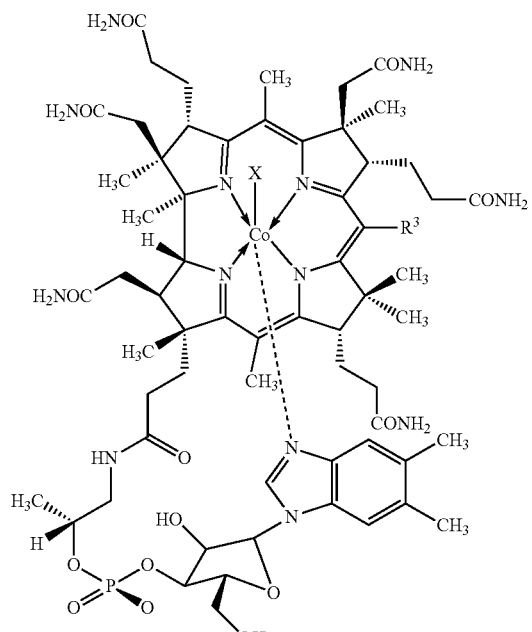

I: X = CN, OH$_2$, OH, Hal (Cl-, Br- I-) or CH$_3$
R$^3$ = H, Hal, (Cl-, Br-, I-), CF$_3$, -alkyl a cobyrinic acid hepta Cl-4 alkyl ester derivative (II), a cobyrinic acid (III) and a cobinamide (IV),

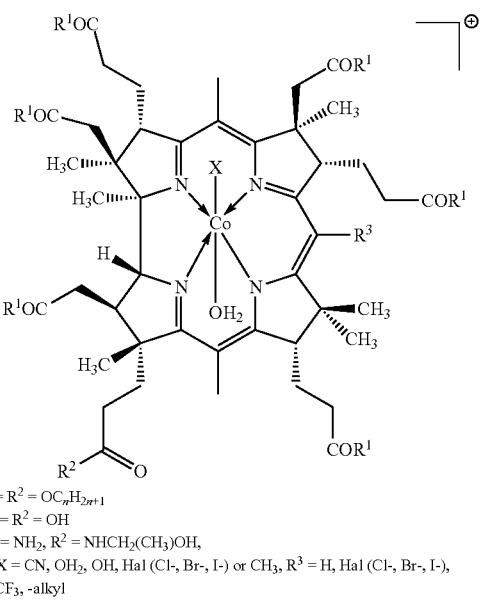

II: R$^1$ = R$^2$ = OC$_n$H$_{2n+1}$
III: R$^1$ = R$^2$ = OH
IV: R$^1$ = NH$_2$, R$^2$ = NHCH$_2$(CH$_3$)OH,
II-IV: X = CN, OH$_2$, OH, Hal (Cl-, Br-, I-) or CH$_3$, R$^3$ = H, Hal (Cl-, Br-, I-), CF$_3$, -alkyl means for passing a gaseous or liquid sample over or across said device, and means for detecting a colour change of said first corrinoid compound.

Particular example of buffers are carbonate, glycine, AMP, AMPD and CHES, more particularly CHES.

In operation, a sample to be tested for cyanide is added to the dried buffer. If interfering metal ions are present, they complex with the buffer and a precipitate forms. The nature and form of this precipitate differs, depending on the nature of the metal ion. However any precipitate formed clearly indicates the presence of interfering ions and that the sample should be treated to liberate cyanide or select different testing procedures, as all metals shown to precipitate with the buffer also complex cyanide.

The method hereinabove described provides a quick and reliable test for metals that can complex cyanide and give a false result. This is an indication either that removal of the offending ions is necessary prior to retesting or choosing an alternative testing and sample preparation method. In the case of precious metals recovery, it can indicate an incomplete result, that is, that there has been an incomplete recovery of the metals from the ore, indicating the possibility of recovering more metal from the ore prior to disposal, and therefore less waste and a more economical result. The disclosure is further described with reference to the following non-limiting examples.

EXAMPLE 1

Preparation & Employment of Solid Buffer

The buffer solutions [Carbonate, Glycine, Boric Acid, AMP, AMPD, CAPSO, NaOH(as reference), CHES] were prepared in a concentration of 0.5 M and 0.25M in water and its pH is set to a value between 9.0 and 10.0 by addition of hydrochloric acid or sodium hydroxide solution. The liquid buffer was filled into plastic vials and dipped into liquid nitrogen, before the vials were closed with perforated lids. The vials were put into a lyophilizer at −83° C. and a pressure of 0.08 mbar. After 12-24 hours, the buffers have dried and were ready for use.

Prior to use, 0.3 ml of the water sample to be tested for cyanide and any potential interferences is added to lyophilized buffer.

EXAMPLE 2

Testing of Interfering Metal Ions

The presence of selected metal ions was simulated by the addition to water of 30, 50, 80, 100, 200, 250, 300, 500 and 1000 ppm of the metal ions shown in the following table. This provided the limits of detection shown in the table.

limit of detection (ppm) for each buffer system with 0.25 M

| Buffer Systems | Metal Ions | | | | | | | |
|---|---|---|---|---|---|---|---|---|
| | $Ni^{2+}$ | $Cu^{2+}$ | $Fe^{2+}$ | $Fe^{3+}$ | $Co^{2+}$ | $Zn^{2+}$ | $Hg^{2+}$ | $Cr^{3+}$ |
| Carbonate | 250 | 100 | 200 | 50 | 200 | 200 | 100 | 100 |
| Glycine | 250 | 100 | 200 | 100 | 250 | 250 | 250 | 250 |
| Boric Acid | 250 | 250 | 250 | 250 | 250 | 250 | 500 | 500 |
| AMP | 250 | 100 | 80 | 80 | 80 | 200 | 100 | 100 |
| AMPD | 200 | 100 | 80 | 80 | 80 | 250 | 250 | 250 |
| CAPSO* | 250 | 250 | 250 | 250 | 250 | 250 | 250 | 250 |
| NaOH | 300 | 300 | 200 | 200 | 500 | 500 | 300 | 300 |
| CHES | 200 | 200 | 100 | 50 | 100 | 200 | 100 | 100 |

*3-(Cyclohexylamino)-2-hydroxy-1-propanesulfonic acid buffer

Similar results were achieved with a higher buffer concentration of 0.5M

To a sample of each of these metal ions in water was added potassium cyanide to give a $CN^-$ concentration of 1.0 ppm. These samples were then added to the dried buffer prepared in Example 1. In each case, there was a coloured or white precipitate, indicating the presence of a metal that had complexed with the $CN^-$.

Had a cyanide-containing sample, also containing any one of these metal ions, been tested by corrinoid-based cyanide detection assay, the cyanide would not have shown up and the tester would have falsely believed that no cyanide was present.

The test indicates that a metal contaminant is present, and that it is necessary to remove it prior to testing for cyanide.

The invention claimed is:

1. A cyanide detection kit comprising:
    (i) a composition for detecting metal contamination comprising a solid buffer, the buffer being adapted to provide a pH of from 9-10; and
    (ii) a cyanide detection component comprising: at least one first colorimetric solid phase extraction device, said first device comprising a non-polar solid phase loaded with a first corrinoid compound selected from the group consisting of: a cobalamine according to formula (I),

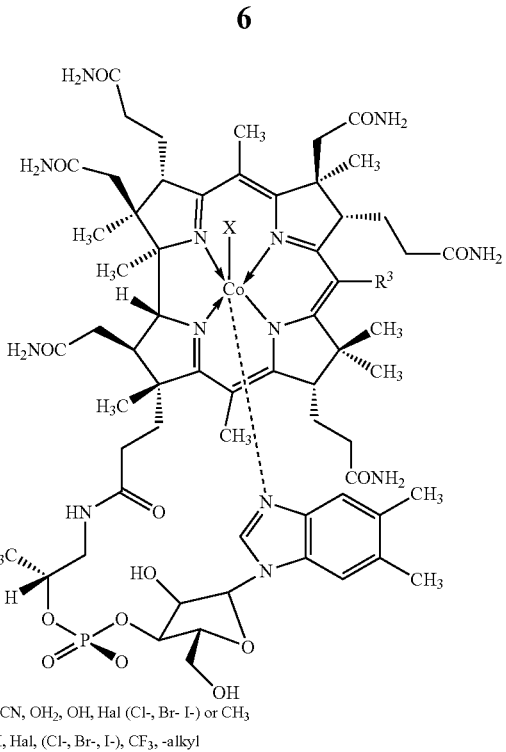

I: X = CN, $OH_2$, OH, Hal (Cl-, Br- I-) or $CH_3$
$R^3$ = H, Hal, (Cl-, Br-, I-), $CF_3$, -alkyl a cobyrinic acid hepta Cl-4 alkyl ester derivative (II), a cobyrinic acid (III) and a cobinamide (IV),

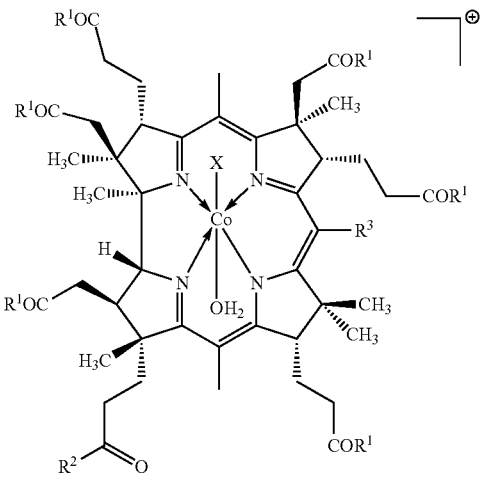

II: $R^1 = R^2 = OC_nH_{2n+1}$,
III: $R^1 = R^2 = OH$
IV: $R^1 = NH_2$, $R^2 = NHCH_2(CH_3)OH$,
II-IV: X = CN, $OH_2$, OH, Hal (Cl-, Br-, I-) or $CH_3$, $R^3$ = H, Hal (Cl-, Br-, I-), $CF_3$, -alkyl 2. The cyanide detection kit according to claim 1, in which the buffer is selected from the group consisting of a N-cyclohexyl-2-aminoethanesulfonic acid (CHES) buffer, Carbonate-Bicarbonate Buffer (Carbonate), Glycine Buffer (Glycine), 2-Amino-2-Methyl-1-Propanol (AMP) buffer, 2-Amino-2-methyl-1,3-propanediol (AMPD) buffer, and combinations thereof.

3. The cyanide detection kit according to claim 2, in which the buffer is CHES.

* * * * *